(12) United States Patent
Matsumoto

(10) Patent No.: US 8,785,367 B2
(45) Date of Patent: Jul. 22, 2014

(54) CLEANSING SHEET

(71) Applicant: Lec, Inc., Tokyo (JP)

(72) Inventor: Michiaki Matsumoto, Tokyo (JP)

(73) Assignee: LEC, Inc., Tokyo (JP)

(*) Notice: Subject to any disclaimer, the term of this patent is extended or adjusted under 35 U.S.C. 154(b) by 0 days.

(21) Appl. No.: 13/712,099

(22) Filed: Dec. 12, 2012

(65) Prior Publication Data

US 2014/0157534 A1    Jun. 12, 2014

(51) Int. Cl.
| | | |
|---|---|---|
| *C11D 17/04* | (2006.01) | |
| *C11D 7/26* | (2006.01) | |
| *C11D 7/32* | (2006.01) | |
| *A61K 8/02* | (2006.01) | |
| *A61K 8/34* | (2006.01) | |
| *A61K 8/40* | (2006.01) | |

(52) U.S. Cl.
USPC ............ 510/438; 510/439; 510/130; 510/131; 510/137; 510/159; 510/504; 510/506; 424/400; 424/401

(58) Field of Classification Search
USPC ......... 510/438, 439, 130, 131, 137, 159, 504, 510/506; 424/400, 401
See application file for complete search history.

(56) References Cited

U.S. PATENT DOCUMENTS

| | | | | |
|---|---|---|---|---|
| 4,741,944 | A | * 5/1988 | Jackson et al. | 428/152 |
| 2002/0002124 | A1* | 1/2002 | Biedermann et al. | 510/218 |
| 2002/0172656 | A1* | 11/2002 | Biedermann et al. | 424/70.21 |
| 2005/0008680 | A1* | 1/2005 | Deckner et al. | 424/443 |
| 2010/0028392 | A1* | 2/2010 | Cawthorne et al. | 424/401 |
| 2013/0230609 | A1* | 9/2013 | Modak et al. | 424/739 |

FOREIGN PATENT DOCUMENTS

JP       2005-296240 A    10/2005

* cited by examiner

*Primary Examiner* — Lorna M Douyon
(74) *Attorney, Agent, or Firm* — Holtz Hotlz Goodman & Chick PC

(57) ABSTRACT

A cleansing sheet including a nonwoven sheet impregnated with a cleaning agent, the cleaning agent containing 99.80 wt % to less than 99.95 wt % of purified water and more than 0.05 wt % to 0.20 wt % of a bactericidal preservative, the bactericidal preservative including more than 0.025 wt % to 0.10 wt % benzalkonium chloride, more than 0.0025 wt % to 0.01 wt % iodopropynyl butylcarbamate, and more than 0.0225 wt % to 0.09 wt % glycol, based on the total weight of the cleaning agent taken as 100 wt %. The cleaning sheet can be applied to the delicate skin of infants or the sensitive skin of elderly people.

3 Claims, No Drawings

CLEANSING SHEET

DETAILED DESCRIPTION OF THE INVENTION

1. Technical Field

The present invention relates to a cleansing sheet composed of a fiber sheet such as a nonwoven fabric impregnated with a cleaning agent.

2. Background Art

Wet cleansing sheets impregnated with cleaning agents have been used to wipe dirty hands and faces, or the bottoms of infants after excretion. Many of the cleaning agents retained in wet cleansing sheets have increased water contents to make wiping easier. The cleaning agents, therefore, contain disinfectants or antibacterial agents to prevent bacterial growth in the water. Furthermore, the wet cleansing sheets, which are used directly on the skin, contain moisturizers such as hyaluronic acid to improve the feel in use.

The cleansing sheets, however, used directly on hands, faces, or the bottoms of infants are desired to include cleaning agents containing reduced amounts of disinfectants or antibacterial agents in view of reducing irritation to skin. The cleansing sheets impregnated with minimum amounts of irritating components, preferably with only plain water are desirable especially for use on the bottoms of infants or sensitive skins of elderly people.

Patent document 1 cited below proposes a cleansing sheet composed of a fiber sheet impregnated with a cleaning agent containing 90 wt % to 98.5 wt % water, 0.03 wt % to 1 wt % bactericidal preservative, 0.5 wt % to 5 wt % alcoholic moisturizer, and 0.05 wt % to 5 wt % aqueous moisturizer relative to the total weight of the cleaning agent.

The conventional cleansing sheets contain 90 wt % to 98.5 wt % water to reduce the contents of the bactericidal preservative, the alcoholic moisturizer, or the water soluble moisturizer, thereby reducing irritation to the skin; hence, infants and people with sensitive skin to chemicals can use them.

CITATION LIST

Patent document

Patent document 1: Japanese Unexamined Patent Application Publication No. 2005-296240

SUMMARY OF INVENTION

Technical Problem

The conventional cleansing sheets, however, allow for bacterial growth caused by distilled or purified water contained in cleaning agents. Accordingly, the water content in the cleaning agent must be reduced to 98.5 wt % so as to make room for a bactericidal preservative. The use of the bactericidal preservative prevents the complete elimination of the irritation to the skin.

The cleansing sheets are used frequently for wiping the bottoms of infants after excretion. Accordingly, users need to take great care about use of the cleansing sheets which may cause eczema or skin rash, especially when used on the delicate skins of infants.

Meanwhile, moisturizers such as alcoholic moisturizers and aqueous moisturizers contained in the cleaning agents can reduce the stickiness on the skin of average persons and thus can improve the feel in use. Such moisturizers, however, can cause skin problems when used by infants with delicate skin or elderly people with sensitive skin.

An object of the invention, which has been accomplished in consideration of such a background, is to provide a cleansing sheet composed of a nonwoven sheet containing a minimized amount of a cleaning agent and applicable to delicate skin of infants or sensitive skin of elderly people.

Solution to Problem

To accomplish the above object, a cleansing sheet comprising a nonwoven sheet impregnated with a cleaning agent is provided, the cleaning agent comprising 99.80 wt % to less than 99.95 wt % purified water and more than 0.05 wt % to 0.20 wt % bactericidal preservative, the bactericidal preservative comprising more than 0.025 wt % to 0.10 wt % benzalkonium chloride, more than 0.0025 wt % to 0.01 wt % iodopropynyl butylcarbamate, and more than 0.0225 wt % to 0.09 wt % glycol based on the total weight of the cleaning agent taken as 100 wt %.

The cleansing sheet as described hereinabove, wherein the glycol is propylene glycol.

The cleansing sheet as described hereinabove, wherein the glycol is 1,3-butylene glycol.

Advantageous Effects of Invention

The cleansing sheet as described hereinabove, which contains 99.80 wt % to less than 99.95 wt % purified water and more than 0.05 wt % to 0.20 wt % bactericidal preservative, based on the total weight of the cleaning agent taken as 100 wt %, can be reliably used for infants and elderly people having delicate skin, without worrying about skin problems owing to the minimized use of the bactericidal preservative, which otherwise could irritate the skin.

The bactericidal preservative, which contains more than 0.025 wt % to 0.10 wt % benzalkonium chloride, more than 0.0025 wt % to 0.01 wt % iodopropynyl butylcarbamate, and more than 0.0225 wt % to 0.09 wt % propylene glycol or 1,3-butylene glycol, can prevent the occurrence and growth of bacteria and fungi regardless of the low content of the bactericidal preservative. Consequently, the cleansing sheets in a sealed package can be stored over a long period of time, and can prevent the occurrence of bacteria and fungi even if the package or cleansing sheet is touched by a hand and ambient air when used.

DESCRIPTION OF EMBODIMENTS

A cleansing sheet in accordance with an embodiment of the present invention will now be described in detail.

The cleansing sheet in accordance with an embodiment of the present invention is composed of a nonwoven sheet impregnated with a cleaning agent. The cleaning agent contains 99.80 wt % to less than 99.95 wt % purified water and more than 0.05 wt % to 0.20 wt % bactericidal preservative based on the total weight of the cleaning agent as 100 wt %. The purified water is prepared in such a way that water is purified with ion exchange resins and was then sterilized with an ultraviolet sterilizer. The resulting purified water has an electrical conductivity, which functions as a measure for an impurity level, of 1 μS/cm or less.

The bactericidal preservative contains more than 0.025 wt % to 0.10 wt % benzalkonium chloride, more than 0.0025 wt % to 0.01 wt % iodopropynyl butylcarbamate, and more than 0.0225 wt % to 0.09 wt % propylene glycol or 1,3-butylene glycol.

Experimental Examples

Based on the experiments conducted by the present inventors, the dependence of antibacterial and antifungal characteristics on the proportion of the purified water contained in the cleaning agent contained in the cleansing sheet of the present invention, benzalkonium chloride, iodopropynyl butylcarbamate, and propylene glycol or 1,3-butylene glycol contained in the bactericidal preservative will be described, in reference to Tables 1 and 2.

Columns 1 to 5 in Table 1 represent the compositions of cleansing agents impregnated in nonwoven fabrics, and Table 2 represents antibacterial and antifungal characteristics of compositions on Columns 1 to 5 in Table 1. The experiments were conducted under the following conditions.
*Antibacterial characteristics: JISL-1902: 2008 'Testing for antibacterial activity and efficacy on textile products'
*Antifungal characteristics: JISZ-2911: 2010 'Methods of test for fungus resistance'
*Bacteria used: Bacterium A: *Escherichia coli* NBRC 3301, Bacterium B: Staphylococcuc aureus NBRC 12732
*Fungi used: Fungus A: *Aspergillus niger* NBRC 6341, Fungus B: Penicilliumcitrinum NBRC 6352, Chaetomiumglobosum NBRC 6347, Myrotheciumverrucaria NBRC 6113

Of the compositions on Columns 1 to 5 in Table 1, Column 1, comparative example, indicates a composition for the cleansing sheet commercially available from the applicant, and Columns 2 to 5 each indicate compositions comprising purified water and bactericidal preservative retained in the cleansing sheets of the present invention.

TABLE 1

|   |   | 1 | 2 | 3 | 4 | 5 |
|---|---|---|---|---|---|---|
| A | Water | 95.7000 | 99.9500 | 99.9000 | 99.8000 | 99.9000 |
| B | Methylparaben | 0.1500 | | | | |
| C | Ethylparaben | 0.0500 | | | | |
| D | Propylparaben | 0.0500 | | | | |
| E | Benzalkonium chloride | 0.0500 | 0.0250 | 0.0500 | 0.1000 | 0.0500 |
| F | Ethanol | | | | | |
| G | Iodopropynyl butylcarbamate | | 0.0025 | 0.0050 | 0.0100 | 0.0050 |
| H | Propylene glycol | 4.0000 | 0.0225 | 0.0450 | 0.0900 | |
| I | 1,3-butylene glycol | | | | | 0.0450 |

(Unit: Wt %)

TABLE 2

|   |   | 1 | 2 | 3 | 4 | 5 |
|---|---|---|---|---|---|---|
| Bacterium A | *Escherichia coli* | — | — | — | — | — |
| Bacterium B | *Stapylococcus aureus* | — | — | — | — | — |
| Fungus A | *Aspergilus niger* | 2 | 1 | 1 | 0-6 | 1 |
| Fungus B | Mixtures of teree species: Peni. Chaeto, and Myroth. | 0-0 | 2 | 0-0 | 0-5 | 0-3 |

*Determination of antibacterial characteristics
(−): the width of the halo is more than 0 mm
(+): the width of the halo is 0 mm
*Determination of antifungal characteristics
0: No mycelial growth was observed in the inoculated portion of the specimen. (The values at the right indicate the width of the growth inhibition expressed in mm)
1: The area of mycelial growth observed in the inoculated portion of the specimen is ⅓ or less of the entire area.
2: The area of mycelial growth observed in the inoculated portion of the specimen is more than ⅓ of the entire area.

The experimental data demonstrates that all the compositions in Columns 1 to 5 had satisfactory antibacterial characteristics. Meanwhile, with respect to antifungal characteristics, the composition in Column 1 (Comparative example: a commercial product) containing 95.70 wt % purified water, 0.15 wt % methylparaben, 0.05 wt % ethylparaben, 0.05 wt % propylparaben, 0.05 wt % benzalkonium chloride, and 4.0 wt % propylene glycol exhibited a growth area of Fungus A to cover more than ⅓ of the entire area. Furthermore, the composition in Column 2 containing 99.95 wt % purified water, 0.025 wt % benzalkonium chloride, 0.0025 wt % iodopropynyl butylcarbamate, and 0.0225 wt % propylene glycol exhibited a growth area of Fungus B to cover more than ⅓ of the entire area. Thus, the compositions on Columns 1 and 2 had poor antifungal characteristics, while having satisfactory antibacterial characteristics.

In contrast, the composition on Column 3 containing 99.90 wt % purified water, 0.05 wt % benzalkonium chloride, 0.005 wt % iodopropynyl butylcarbamate, and 0.045 wt % propylene glycol, exhibited a growth area of Fungus A to cover ⅓ or less of the entire area. The composition on Column 4 containing 99.80 wt % purified water, 0.1 wt % benzalkonium chloride, 0.01 wt % iodopropynyl butylcarbamate, and 0.09 wt % propylene glycol exhibited no growth of Fungus A and Fungus B and widths of the growth inhibitions of 5 to 6 mm. Furthermore, the composition on Column 5 containing 99.90 wt % purified water, 0.05 wt % benzalkonium chloride, 0.005 wt % iodopropynyl butylcarbamate, and 0.045 wt % 1,3-butylene glycol exhibited an area of the growth of Fungus A to cover ⅓ or less of the entire area and a width of the growth inhibition of Fungus B of 3 mm. Thus, the compositions on Columns 3 to 5 had satisfactory antibacterial and antifungal characteristics.

The cleansing sheet according to the embodiment described above, which contains more than 0.05 wt % to 0.20 wt % of a bactericidal preservative composed of benzalkonium chloride, iodopropynyl butylcarbamate, and propylene glycol or 1,3-butylene glycol based on the total weight of the cleaning agent taken as 100 wt %, exhibits sufficient antibacterial characteristics and antifungal characteristics regardless of such a small content of bacterial preservative, and thus can contain 99.80 wt % to less than 99.95 wt % purified water. Thus, the bactericidal preservative, which is irritant to the skin, can be minimized so as to be used reliably for infants and elderly people having delicate skin without worrying about skin problems.

Furthermore, even a small content of the bactericidal preservative relative to the total cleaning agent, which contains more than 0.025 wt % to 0.10 wt % benzalkonium chloride, more than 0.0025 wt % to 0.01 wt % iodopropynyl butylcarbamate, and more than 0.0225 wt % to 0.09 wt % propylene glycol or 1,3-butylene glycol, can prevent the occurrence of *Escherichia coli*, *Staphylococcus aureus*, and fungi as shown in the experimental examples above. Consequently, the cleansing sheet in a sealed package can be stored over a long period of time, and can prevent the occurrence of bacteria and fungi even if a hand or ambient air touches the package or the cleansing sheet in use.

The present invention is not limited to the embodiments described above on nonwoven fabrics impregnated with purified water and bactericidal preservatives. For example, the nonwoven fabrics can be sterilized by any other means such as irradiation with UV light before being impregnated with purified water and bactericidal preservative. In this case, the original nonwoven fabric is sterilized and then is cut to be impregnated with purified water and bactericidal preservative.

INDUSTRIAL APPLICABILITY

The cleansing sheet of the present invention is applicable to wiping dirty hands and faces, or wiping the bottoms of infants.

The invention claimed is:

1. A cleansing sheet comprising a nonwoven sheet impregnated with a cleaning agent,
    the cleaning agent consisting of 99.80 wt % to less than 99.95 wt % of purified water and more than 0.05 wt % to 0.20 wt % of a bactericidal and/or a fungicidal preservative,
    the bactericidal and/or the fungicidal preservative consisting of more than 0.025 wt % to 0.10 wt % benzalkonium chloride, more than 0.0025 wt % to 0.01 wt % iodopropynyl butylcarbamate, and more than 0.0225 wt % to 0.09 wt % glycol based on the total weight of the cleaning agent taken as 100 wt %.

2. The cleansing sheet according to claim 1, wherein the glycol is propylene glycol.

3. The cleansing sheet according to claim 1, wherein the glycol is 1,3-butylene glycol.

* * * * *